United States Patent [19]

Hinding

[11] 4,326,549
[45] Apr. 27, 1982

[54] DENTAL HYGIENE APPLIANCE

[76] Inventor: John H. Hinding, 1140 S. Robert St., West St. Paul, Minn. 55118

[21] Appl. No.: 178,947

[22] Filed: Aug. 18, 1980

[51] Int. Cl.$^3$ .............................................. A61C 15/00
[52] U.S. Cl. ................................................ 132/92 R
[58] Field of Search .................. 132/89, 90, 91, 92 R, 132/92 A; 433/105, 141

[56] References Cited

U.S. PATENT DOCUMENTS

| | | | |
|---|---|---|---|
| 1,147,594 | 7/1915 | Ball | 433/125 |
| 2,450,635 | 10/1948 | Dombouski | 132/92 A |
| 3,368,279 | 2/1968 | Weissman | 433/105 |
| 3,667,483 | 6/1972 | McCabe | 132/92 A |
| 3,847,167 | 11/1974 | Brien | 132/92 R |

Primary Examiner—Robert Peshock
Attorney, Agent, or Firm—Kinney, Lange, Braddock, Westman and Fairbairn

[57] ABSTRACT

A device for applying dental floss between the teeth including a frame having a handle and a trigger. A motor and drive shaft is mounted in the frame, including motor control means operably connected to the trigger and power source means for supplying power to the motor. A drive wheel and a plurality of guide pulleys are positioned in the frame to define a path for a closed loop of dental floss under suitable tension. The path includes an open span sized to permit passage of the dental floss between a person's teeth. The drive wheel is positioned to engage the drive shaft to cause rotation of the wheel by the motor.

In a preferred embodiment, the frame includes a first portion mounting the motor to permit the drive shaft to extend outward from the first portion of the frame and a second portion mounting the guide pulleys and the drive wheel to position the dental floss loop. The second portion has a drive shaft receiving opening positioned to permit the drive shaft to engage the drive wheel upon insertion of the shaft into the opening. Mounting means removably mounting the first and second portions to one another in a drive shaft engaging position is provided. In a preferred embodiment, the mounting means includes a pair of bayonet rods mounted on the first portion of the frame extending outward in triangular relationship with the drive shaft and the second portion of the frame defines a pair of bayonet accepting means which hold the two parts of the frame together during operation.

9 Claims, 7 Drawing Figures

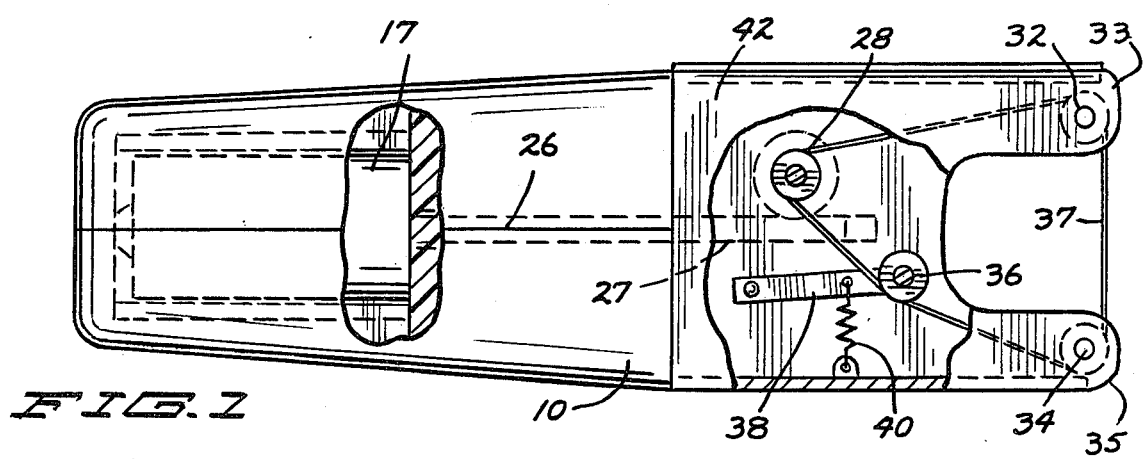
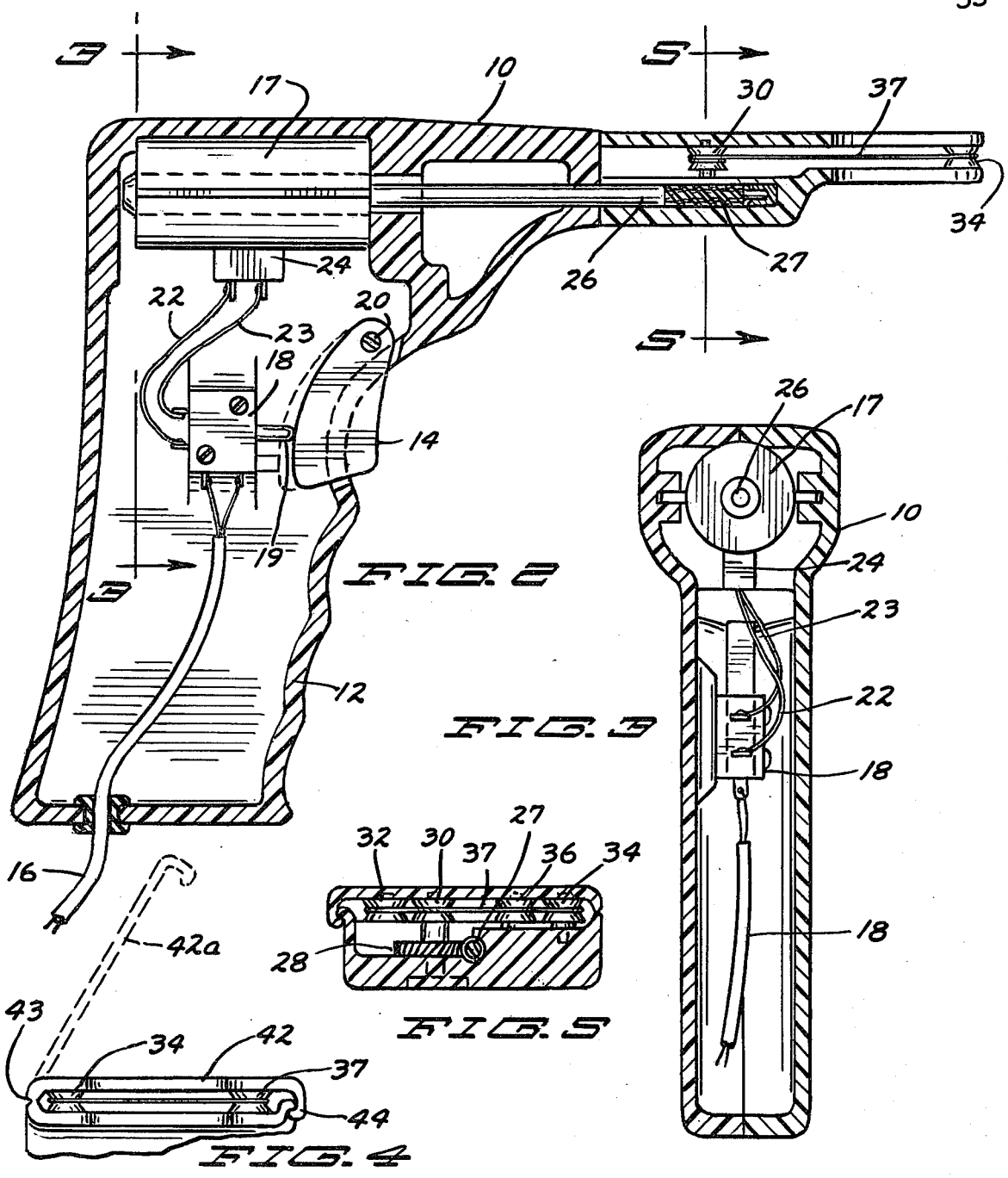

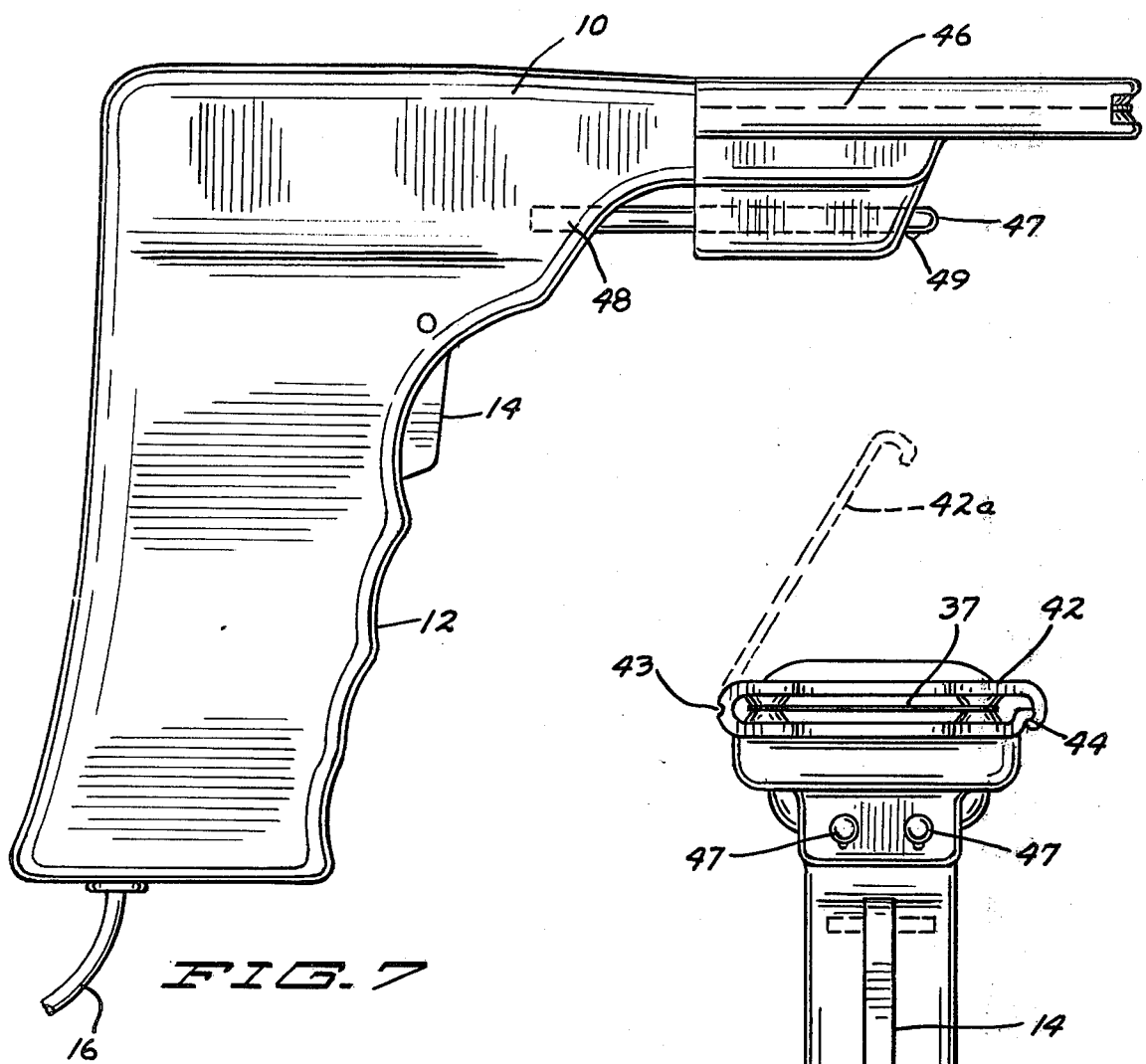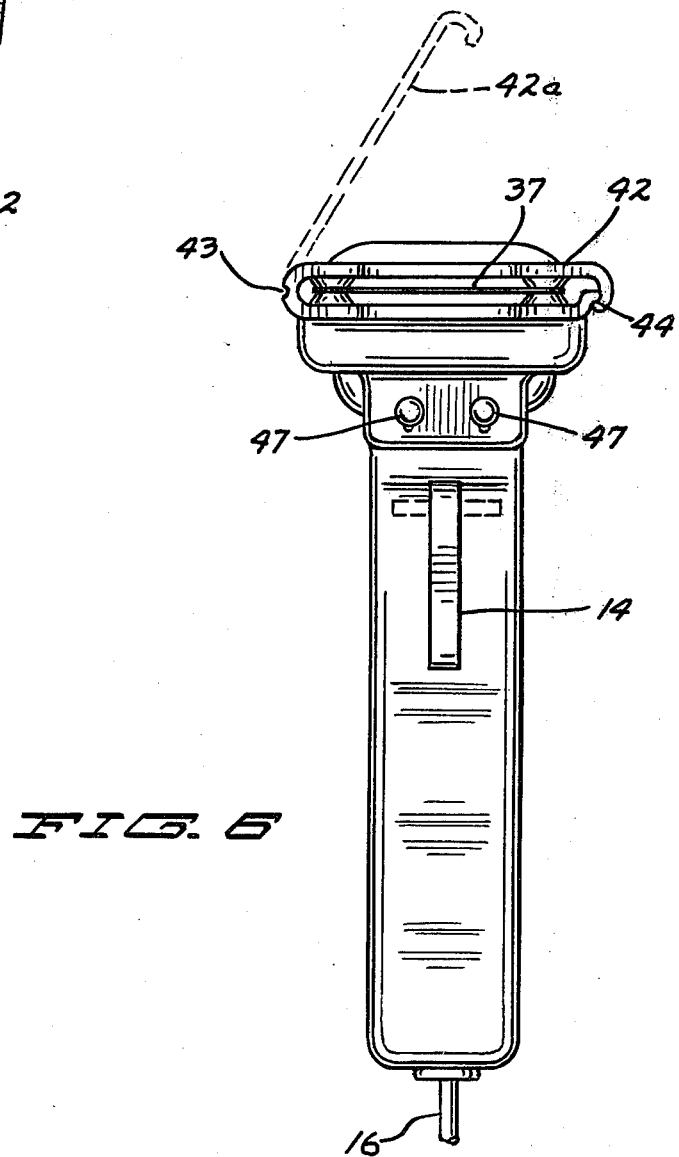

DENTAL HYGIENE APPLIANCE

BACKGROUND OF THE INVENTION

The use of dental floss as part of a regular health maintenance program for dental hygiene has been proven to be extremely effective in helping minimize dental problems. Nevertheless, not as many people use dental floss as would be benefited by its use. Among the reasons why dental floss is not more universally used is the inconvenience and trouble of using dental floss without the assistance of mechanical aids.

Various devices have been proposed to assist in the use of dental floss. Among these is the device shown in British Pat. No. 778,564 which discloses a tooth cleaning device wherein the dental floss is looped around a forked end of a device and hook on a lug for adjustable tension. The device is hand powered.

U.S. Pat. No. 1,147,594 discloses a dental tool in which an endless band of finishing strips is mounted in a pulley system which is held by hand.

U.S. Pat. No. 3,667,483 teaches a dental floss reciprocator embodying a pair of arms projecting from a support frame and spaced from each other to receive teeth therebetween. Guides at the outer ends of the arms receive and permit relative movement of floss passing from a supply reel to a takeup reel. Forward and rearward angular movement imparted alternately to the reels with forward movement greater than the rearward movement to reciprocate and move the floss progressively to take up reels is disclosed.

U.S. Pat. No. 3,822,432 discloses a rotary tooth cleaning device which is drivably secured to the end of a hand held power drive shaft with a self-contained motor. No description of dental floss is suggested in this patent.

U.S. Pat. No. 3,847,167 discloses a reciprocating power driven device for holding and moving a ring of dental floss which is positioned to have access to the mouth. The ring of floss is advanced to bring a clean section into the area between the arms manually after the idle pulley is retracted. Neither of these devices shown in these last two patents show the continuous rotation of a loop of dental floss material under controlled tension to effectively clean the areas between the teeth.

The foregoing patents were located in a preliminary search. Applicant and those in privity with him know of no closer prior art than that set out above; and they know of no prior art which anticipates the claim made in this application.

SUMMARY OF THE INVENTION

The present invention relates to a device for applying dental floss between the teeth. The device includes a frame having a handle grip and a trigger. Motor and drive shaft means are mounted in the frame and include motor control means operably connected to the trigger and power source means for supplying power to the motor. A drive wheel and a plurality of guide pulleys are positioned in said frame to define a path for a closed loop of dental floss under tension. This path includes an open span sized to admit passage of the floss between a person's teeth. The drive wheel is positioned to engage the drive shaft to cause rotation of the wheel by the rotor at a tension in the floss which is adequate to effectively clean between the teeth.

In a preferred embodiment, the drive shaft includes a worm gear and a drive wheel includes a spur gear sized to engage the worm gear. Also preferred is a frame which includes a first portion mounting the motor to permit the drive shaft to extend outward from the first portion of the frame and a second portion which is separate and distinct from the first portion and which mounts the guide pulleys and the drive wheel to position the floss loop. This second portion has a drive shaft to engage the drive wheel upon insertion of the shaft into the opening. Mounting means are provided for removably mounting the first and second portions of the frame in drive shaft engaging position.

A preferred method of mounting the first and second portions of the frame includes the use of a plurality of bayonet means on one of the portions and bayonet accepting means on the other portion so that the two portions fit together. In one embodiment, the plurality of bayonet means may comprise a pair of bayonet rods mounted on the first portion of the frame extending outward in a triangular relationship with said drive shaft. The second portion of the frame defines a pair of bayonet accepting means so that the drive shaft and the two bayonet rods form a triangular support for the two portions. At least one bayonet rod may extend completely through the second portion of the frame to facilitate separation of the two framed portions.

In one embodiment of the present invention, the frame includes a cover means removably covering the path so that upon opening the cover, the closed loop of floss may be replaced. Also preferred is to include a tension pulley biasing against the closed loop of floss among the plurality of guide pulleys so as to maintain a desired tension in the loop. The biasing means, which may be a spring, is sufficient to prevent slippage of the loop upon use unless a substantial pressure is applied against the loop.

IN THE DRAWINGS

FIG. 1 is a top elevational view partially cut away of one embodiment of the present invention;

FIG. 2 is a sectioned view of the side of the device shown in FIG. 1;

FIG. 3 is a view along line 3—3 of FIG. 2;

FIG. 4 is a partial view of the end of the device shown in FIG. 2;

FIG. 5 is a view along line 5—5 in FIG. 2;

FIG. 6 is a front view of a preferred embodiment of the present invention; and

FIG. 7 is a side view of the device shown in FIG. 6.

DESCRIPTION OF PREFERRED EMBODIMENT

As shown in the various figures, a device for applying dental closs between the teeth includes a frame 10 which has a grip 12 and a trigger 14. A source of electrical power is connected by electrical conductors 16 to switch 18 via toggle 19 so that pivoting of trigger 14 about pivot 20 will cause current to flow through conductors 22 and 23 to connector 24 of motor 17.

Motor 17 turns drive shaft 26 which includes worm gear 27 mounted on the end thereof. Worm gear 27 engages drive wheel 28, as can be seen in FIG. 5. Motor 17 is a variable speed motor, the speed of worm gear 27 and therefore drive wheel 28 can be varied by means of trigger 14 to vary the speed of the dental floss.

Drive wheel 28 is connected to drive wheel pulley 30 which also is positioned in cooperation with guide pulleys 32 and 34 and tension pulley 36 to define a path for the dental floss 37. Pulleys 32 and 34 are spaced apart to define an open span sized to permit passage of the floss 37 between a person's teeth. Edges 33 and 35 protect the mouth from the turning pulleys. Beam 38 and spring 40 provide tension on tension pulley 36 in an amount which is calibrated to permit the floss 37 to adequately clean between the teeth.

To permit access to the floss loop 37, which must be changed from time to time, a preferred embodiment includes a flip top portion 42 of the frame 10. Top 42 is hinged at 43 and maintained in a closed position at latch snap 44. If the frame 10 and the top 42 are constructed from plastic, hinge 43 may be what is known as a "living hinge", thereby permitting ease of manufacture.

FIGS. 6 and 7 illustrate a preferred embodiment in which the frame 10 has a head portion 46 which may be detached from the main body of the frame 10. Bayonet 47 is mounted to the frame 10 at position 48 and extends through the detachable portion 46. Restrainer 49 prevents slippage of the bayonet 47 to accidentally separate the detachable portion 46 from the frame 10. Insertion of the bayonets 47 and the drive shaft 26 with a worm gear 27 will cause the worm gear 27 to engage spur gear or drive wheel 28 which will cause slight rotation of the floss 37 of the pulley path. Each member of a family can easily have their own detachable head 46, so that the only one motor and main frame 10 needs to be purchased.

Detachable head 46 may have the flip top portion 42 and hinge 43 with snap 44 to permit rapid changing of the dental floss loop 37. Alternatively, the head 46 may be cast from an inexpensive material and may be detachable and a throwaway of recyclable material.

The embodiments of the invention in which an exclusive property or privilege is claimed are defined as follows:

1. A device for applying and moving a closed loop of dental floss between the teeth, comprising:
   A. a closed loop of dental floss;
   B. a frame having a first portion including handle grip and a trigger, and a second portion extending outwardly from the first portion at approximately right angles thereto;
   C. motor and drive train means mounted in said first portion of said frame, including motor control means operably connected to said trigger and power source means for supplying power to said motor to rotate the drive train means, said drive train means including a drive shaft extending outwardly from said first portion and into said second portion of said frame, said drive shaft including a worm gear at its outer end; and
   D. guide means including a drive wheel and a plurality of guide pulleys positioned in said second portion of said frame to define a path for said closed loop of dental floss under tension, said path including an open span sized to permit passage of said floss between a person's teeth, said drive wheel including a spur gear positioned to engage said drive shaft worm gear to cause rotation of said drive wheel by said motor.

2. The device of claim 1 wherein:
   D. said frame includes cover means removably covering said path to permit replacement of said closed loop of floss.

3. The device of claim 1 wherein:
   D. said plurality of guide pulleys includes a tension pulley biased against said loop to maintain desired tension in said loop.

4. The device of claim 3 wherein:
   E. said bias is sufficient to prevent slippage unless substantial pressure is applied against said loop.

5. A device for applying dental floss between the teeth, comprising:
   A. a frame having a handle grip and a trigger;
   B. a motor and drive shaft mounted in said frame, including motor control means operably connected to said trigger and power source means for supplying power to said motor to rotate the drive shaft;
   C. a drive wheel and a plurality of guide pulleys positioned in said frame to define a path for a closed loop of dental floss under tension, said path including an open span sized to permit passage of said floss between a person's teeth, said drive wheel being positioned to engage said drive shaft to cause rotation of said drive wheel by said motor;
   D. said frame including a first portion mounting said motor to permit said drive shaft to extend outward from said first portion of said frame;
   E. said frame including a second portion mounting said guide pulleys and said drive wheel to position said floss loop, said second portion having a drive shaft receiving opening positioned to permit said drive shaft to engage said drive wheel upon insertion of said shaft in said opening; and
   F. mounting means removably mounting said first and second portions of said frame in said drive shaft engaging position.

6. The device of claim 5 wherein:
   G. said drive shaft includes a worm gear and said drive wheel includes a spur gear sized to engage said worm gear.

7. The device of claim 5 wherein:
   G. said mounting means includes a plurality of bayonet means on one of said portions and bayonet accepting means on the other of said portions.

8. The device of claim 7 wherein:
   H. said plurality of bayonet means comprises a pair of bayonet rods mounted on said first portion of said frame extending outward in triangular relationship with said shaft and said second portion of said frame defines a pair of bayonet accepting means positioned to receive said bayonet rods.

9. The device of claim 7 wherein:
   H. at least one of said bayonet rods extends through said second portion of said frame to facilitate separation of said frame portions.

* * * * *